(12) United States Patent
Huwyler et al.

(10) Patent No.: US 7,119,113 B2
(45) Date of Patent: *Oct. 10, 2006

(54) OXAZOLES AS MGLUR1 ENHANCERS

(75) Inventors: Joerg Huwyler, Burg (CH); Frederic Knoflach, Arlesheim (CH); Eric Vieira, Allschwil (CH); Juergen Wichmann, Steinen (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 93 days.

This patent is subject to a terminal disclaimer.

(21) Appl. No.: 10/740,245

(22) Filed: Dec. 18, 2003

(65) Prior Publication Data
US 2004/0132792 A1 Jul. 8, 2004

(30) Foreign Application Priority Data
Dec. 23, 2002 (EP) ................... 02028747

(51) Int. Cl.
*A61K 31/421* (2006.01)
*C07D 263/30* (2006.01)
(52) U.S. Cl. ............... 514/377; 548/215; 548/233; 514/374
(58) Field of Classification Search ........... 548/215, 548/233; 514/377, 374
See application file for complete search history.

(56) References Cited

U.S. PATENT DOCUMENTS 6,462,198 B1 * 10/2002 Bleicher et al. ............ 548/131
6,596,743 B1 * 7/2003 Bleicher et al. ............ 514/364
6,803,381 B1 * 10/2004 Bleicher et al. ............ 514/454

FOREIGN PATENT DOCUMENTS

WO WO 00/63166 10/2000

OTHER PUBLICATIONS

Knoflach et al., Proc. Nat. Acad. Sci. USA vol. 98: 13402-13407 (2001).
Schlaeger et al., New Dev. New Appl. Anim. Cell Techn. Proc. ESACI Meet. vol. 15 (1998) pp. 105-112 & 117-120.
Houston Biochem. Pharmacol. vol. 47 No. 9, pp. 1469-1479 (1994).
Crank & Foulis, J. Med. Chem. vol. 14: pp. 1075-1077 (1971).
Saha et al. J. Am. Chem. Soc. 111 p. 4856-4859 (1989).

* cited by examiner

*Primary Examiner*—Golam M. M. Shameem
(74) *Attorney, Agent, or Firm*—George W. Johnson; Patricia S. Rocha-Tramaloni; Kimberly J. Prior

(57) ABSTRACT

The invention relates to carboxamide derivatives as defined in the specification and claims, to a process for their preparation, to pharmaceutical compositions comprising them and to their use as mGluR1 enhancers in the treatment and prevention of neurological disorders and diseases, such as Alzheimer's disease and dementia.

21 Claims, No Drawings

OXAZOLES AS MGLUR1 ENHANCERS

FIELD OF THE INVENTION

This invention relates to carboxamide derivatives, to a process for their preparation, and to pharmaceutical compositions comprising them. These compounds are mGluR1 enhancers and, therefore, are useful for treating central nervous system diseases, such as Alzheimer's disease, Parkinson's disease, Huntingdon chorea, amyotrophic lateral sclerosis (ALS) and dementia.

BACKGROUND OF THE INVENTION

In the central nervous system (CNS) the transmission of stimuli takes place by the interaction of a neurotransmitter, which is sent out by a neuron, with a neuroreceptor. L-glutamic acid, the most commonly occurring neurotransmitter in the CNS, plays a critical role in a large number of physiological processes. The glutamate-dependent stimulus receptors are divided into two main groups. The first main group forms ligand-controlled ion channels. The metabotropic glutamate receptors (mGluRs) belong to the second main group and, furthermore, belong to the family of G-protein-coupled receptors. At present, eight different members of these mGluRs' are known and of these some even have sub-types. On the basis of structural parameters, the different second messenger signaling pathways and the different affinity to low-molecular weight chemical compounds, these eight receptors can be sub-divided into three sub-groups: mGluR1 and mGluR5 belong to group I, mGluR2 and mGluR3 belong to group II and mGluR4, mGluR6, mGluR7 and mGluR8 belong to group III. Ligands of metabotropic glutamate receptors belonging to the first group can be used for the treatment or prevention of acute and/or chronic neurological disorders such as psychosis, schizophrenia, Alzheimer's disease, cognitive disorders and memory deficits, as well as chronic and acute pain. Other treatable indications in this connection are restricted brain function caused by bypass operations or transplants, poor blood supply to the brain, spinal cord injuries, head injuries, hypoxia caused by pregnancy, cardiac arrest and hypoglycaemia. Further treatable indications are Huntington's chorea, amyotrophic lateral sclerosis (ALS), dementia caused by AIDS, eye injuries, retinopathy, idiopathic parkinsonism or parkinsonism caused by medicaments as well as conditions which lead to glutamate-deficiency functions, such as e.g. muscle spasms, convulsions, migraine, urinary incontinence, nicotine addiction, opiate addiction, anxiety, vomiting, dyskinesia and depression. Indications which are potentially treatable with mGluR1 agonists include Alzheimer's disease, cognitive disorders and memory deficits, Huntington's chorea, amyotrophic lateral sclerosis (ALS), and dementia.

Selective positive allosteric modulators (enhancers) of mGlu1 receptors are compounds which do not directly activate mGlu1 receptors by themselves, but binding of these compounds increase the affinity of a glutamate-site agonist at its extracellular N-terminal binding site. Positive allosteric modulation is an attractive mechanism for enhancing appropriate physiological receptor activation, and the results obtained in cerebellar slices strongly suggest that mGluR1 enhancers can modulate physiological mGlu1 activity in the brain [Knoflach et al., Proc. Nat. Acad. Sci. USA 98:13402–13407 (2001)] by increasing the affinity of a glutamate-site agonist at its extracellular N-terminal binding site. Selective mGluR1 enhancers therefore possess important therapeutic utility and their discovery opens the possibility for therapeutically relevant positive modulation of mGlu1 receptors.

SUMMARY OF THE INVENTION

An object of the present invention therefore is to provide compounds which have the advantageous properties mentioned above and are therefore useful in the prevention and treatment of the above mentioned diseases.

Thus, the present invention provides a compound of formula I

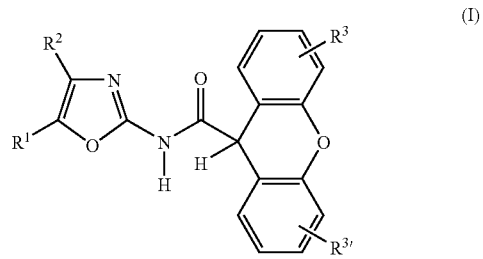

wherein
one of $R^1$ and $R^2$ is trifluoromethyl, and the other is hydrogen;
$R^3$ and $R^{3'}$ are each independently hydrogen or halogen;
and pharmaceutically acceptable salts thereof.

It has been found that the compounds of formula I and their pharmaceutically acceptable salts are mGluR I enhancers. Thus, the present invention also provides pharmaceutical compositions containing a compound of formula I or a pharmaceutically acceptable salt thereof and a pharmaceutically acceptable carrier. The invention further provides methods for enhancing mGluR1 and treating central nervous diseases as defined herein by administering a therapeutically effective amount of a compound of the invention.

The present invention further provides a process for the manufacture of the compounds of the invention and pharmaceutically acceptable salts thereof.

DESCRIPTION OF THE INVENTION

The present invention provides compounds of formula I and their pharmaceutically acceptable salts. The invention also provides processes for the manufacture of the compounds. The invention further provides compositions containing the compounds of the invention and methods for enhancing mGluR1 and treating central nervous system diseases.

In a first aspect the present invention provides a compound of formula I

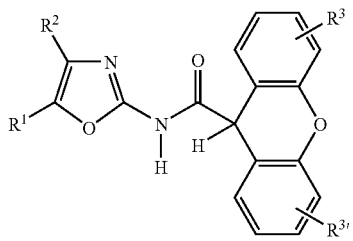

wherein
one of $R^1$ and $R^2$ is trifluoromethyl, and the other is hydrogen;
$R^3$ and $R^{3'}$ each indiependently are hydrogen or halogen;
or a pharmaceutically acceptable salt thereof.

The compounds of formula I are new. They are described generically in PCT patent application No. WO 00/63166 (F. Hoffmann-La Roche AG).

"Pharmaceutically acceptable salts" of a compound means salts that are pharmaceutically acceptable, which are generally safe, non-toxic, and neither biologically nor otherwise undesirable, and that possess the desired pharmacological activity of the parent compound. These salts are derived from an inorganic or organic acid or base. If possible, Active Compounds may be converted into pharmaceutically acceptable salts. It should be understood that all references to pharmaceutically acceptable salts include solvent addition forms (solvates) or crystal forms (polymorphs) of the same acid addition salt.

Preferred compounds of formula I in the scope of the present invention are for example those, wherein $R^3$ and $R^{3'}$ are hydrogen.

These are the following compounds:
9H-xanthene-9-carboxylic acid (4-trifluoromethyl-oxazol-2-yl)-amide, and
9H-xanthene-9-carboxylic acid (5-trifluoromethyl-oxazol-2-yl)-amide.

Further preferred compounds of formula I are those, wherein $R^1$ is trifluoromethyl and $R^2$ is hydrogen.

Especially preferred are compounds of formula I, wherein $R^1$ is trifluoromethyl, $R^2$ is hydrogen, and wherein at least one of $R^3$ or $R^{3'}$ is halogen. More preferably, at least one of $R^3$ or $R^{3'}$ is fluoro. In one aspect, $R^1$ is trifluoromethyl, $R^2$ is hydrogen, and at least one of $R^3$ or $R^{3'}$ is fluoro.

The following compounds are examples thereof:
2-fluoro-9H-xanthene-9-carboxylic acid (5-trifluoromethyl-oxazol-2-yl)-amide,
3-fluoro-9H-xanthene-9-carboxylic acid (5-trifluoromethyl-oxazol-2-yl)-amide,
4-fluoro-9H-xanthene-9-carboxylic acid (5-trifluoromethyl-oxazol-2-yl)-amide,
2,7-difluoro-9H-xanthene-9-carboxylic acid (5-trifluoromethyl-oxazol-2-yl)-amide, and
3,6-difluoro-9H-xanthene-9-carboxylic acid (5-trifluoromethyl-oxazol-2-yl)-amide.

Further preferred are compounds of formula I, wherein $R^2$ is trifluoromethyl and $R^1$ is hydrogen.

Especially preferred are compounds of formula I, wherein $R^2$ is trifluoromethyl, $R^1$ is hydrogen, and wherein at least one of $R^3$ or $R^{3'}$ is halogen. More preferably, at least one of $R^3$ or $R^{3'}$ is fluoro. In one aspect, $R^1$ is hydrogen, $R^2$ is trifluoromethyl, and at least one of $R^3$ or $R^{3'}$ is fluoro.

Examples thereof are the following compounds:
2-fluoro-9H-xanthene-9-carboxylic acid (4-trifluoromethyl-oxazol-2-yl)-amide,
3-fluoro-9H-xanthene-9-carboxylic acid (4-trifluoromethyl-oxazol-2-yl)-amide,
3-fluoro-9H-xanthene-9-carboxylic acid (4-trifluoromethyl-oxazol-2-yl)-amide,
2,7-difluoro-9H-xanthene-9-carboxylic acid (4-trifluoromethyl-oxazol-2-yl)-amide, and
3,6-difluoro-9H-xanthene-9-carboxylic acid (4-trifluoromethyl-oxazol-2-yl)-amide.

Also preferred are compounds of formula I, wherein $R^2$ is trifluoromethyl, $R^1$ is hydrogen, and wherein at least one of $R^3$ or $R^{3'}$ is chloro.

The following compounds are examples thereof:
2-chloro-9H-xanthene-9-carboxylic acid (4-trifluoromethyl-oxazol-2-yl)-amide, and
4-chloro-9H-xanthene-9-carboxylic acid (4-trifluoromethyl-oxazol-2-yl)-amide.

The invention embraces all stereoisomeric forms in addition to the racemates.

The term "halogen" embraces fluorine, chlorine, bromine and iodine.

The compounds of general formula I and their pharmaceutically acceptable salts can be manufactured by a process, which comprises reacting a compound of formula II

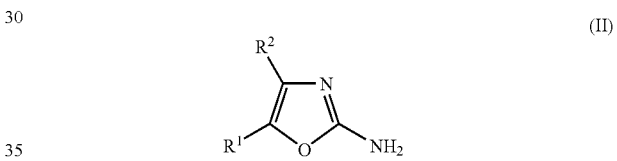

wherein one of $R^1$ and $R^2$ is trifluoromethyl, and the other one is hydrogen, with a compound of formula III

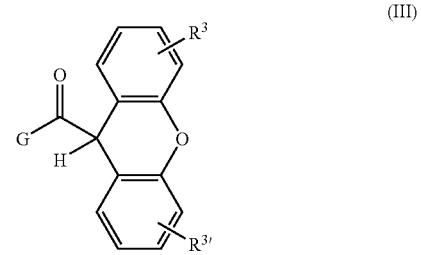

wherein $R^3$ and, $R^{3'}$ are each independently hydrogen or halogen, and G is chloro or hydroxy, to obtain a compound of formula I

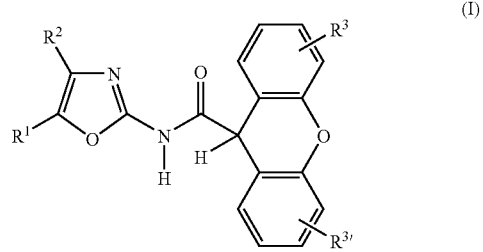

and, if desired, converting a compound of formula I into a pharmaceutically acceptable salt.

In accordance with this process, compounds of formula I may be prepared by a reaction of an oxazol-2-ylamine of formula II with a carboxylic acide chloride of formula IIIa in the presence of N,N-dimethylamino pyridine at a temperature of 0° C. The preferred solvent is methylene chloride (scheme 1).

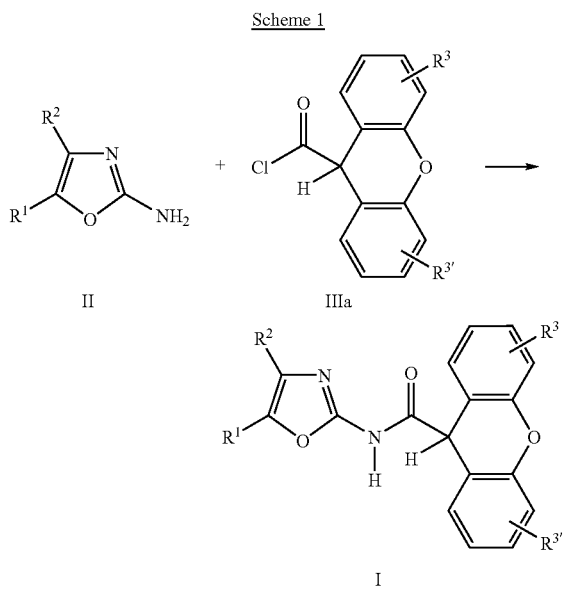

Alternatively, compounds of formula I may be prepared by a reaction of an oxazol-2-ylamine of formula II with a xanthene-9-carboxylic acide of formula IIIb. The carboxylic acid is activated with 1,1'-carbonylbis(3-methylimidazolium)triflate (CBMIT) in nitromethane at a temperature of 10° C. After warming up to room temperature the amine is added (scheme 2).

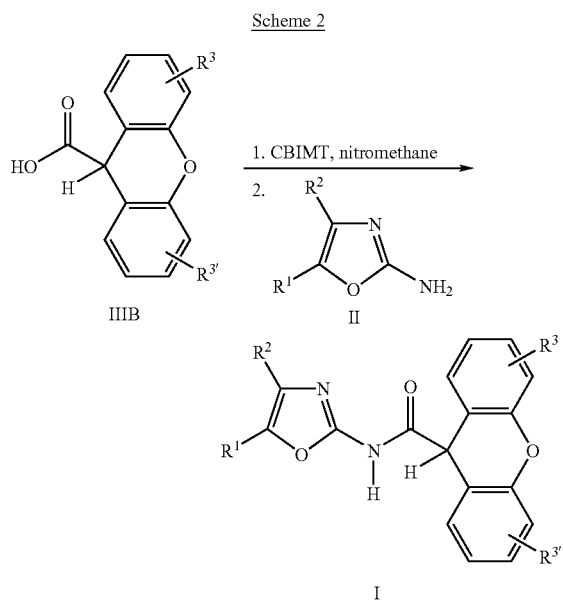

The pharmaceutically acceptable salts can be manufactured readily according to methods known per se and taking into consideration the nature of the compound to be converted into a salt. Inorganic or organic acids such as, for example, hydrochloric acid, hydrobromic acid, sulphuric acid, nitric acid, phosphoric acid or citric acid, formic acid, fumaric acid, maleic acid, acetic acid, succinic acid, tartaric acid, methanesulphonic acid, p-toluenesulphonic acid and the like are suitable for the formation of pharmaceutically acceptable salts of basic compounds of formula I. Compounds which contain the alkali metals or alkaline earth metals, for example sodium, potassium, calcium, magnesium or the like, basic amines or basic amino acids are suitable for the formation or pharmaceutically acceptable salts of acidic compounds.

All starting materials employed in the processes described herein are either commercially available or can be prepared by conventional means.

It has been surprisingly found that the compounds of formula I are mGlu 1 receptor agonists and positive allosteric modulators (enhancers) of metabotropic glutamate 1 (mGlu 1) receptors. Thus, the compounds of the invention and their pharmaceutically acceptable salts can be used for the treatment or prevention of acute and/or chronic neurological disorders, such as psychosis, schizophrenia, Alzheimer's disease, cognitive disorders and memory deficits, as well as acute and chronic pain. Other treatable indications are restricted brain function caused by bypass operations or transplants, poor blood supply to the brain, spinal cord injuries, head injuries, hypoxia caused by pregnancy, cardiac arrest and hypoglycaemia. Further treatable indications are Alzheimer's disease, Huntington's chorea, ALS, dementia caused by AIDS, eye injuries, retinopathy, idiopathic parkinsonism or parkinsonism caused by medicaments as well as conditions which lead to glutamate-deficient functions, such as e.g. muscle spasms, convulsions, migraine, urinary incontinence, nicotine addiction, psychoses, opiate addiction, anxiety, vomiting, dyskinesia and depression.

The compounds of the present invention are group I mGlu receptor agonists. The compounds show activities, as measured in the below binding assay, of 0.2 μM or less.

Binding Assay cDNA encoding rat mGlu 1a receptor obtained from Prof. S. Nakanishi (Kyoto, Japan) was transiently transfected into EBNA cells using a procedure described by Schlaeger et al, New Dev. New Appl. Anim. Cell Techn., Proc. ESACT Meet., 15, (1998), 105–112 and 117–120. $[Ca^{2+}]i$ measurements were performed on mGlu 1a transfected EBNA cells after incubation of the cells with Fluo-3 AM (0.5 μM final concentration) for 1 hour at 37° C. followed by 4 washes with assay buffer (DMEM supplemented with Hank's salt and 20 mM HEPES. $[Ca^{2+}]i$ measurements were done using a fluorometric imaging plate reader (FLIPR, Molecular Devices Corporation, La Jolla, Calif., USA). When compounds were evaluated as antagonists they were tested against 10 μM glutamate as agonist.

The activation (agonists) curves were fitted with a four parameter logistic equation giving $EC_{50}$, and Hill coefficient using the iterative non linear curve fitting software Origin (Microcal Software Inc., Northampton, Mass., USA).

In the table below are shown specific $EC_{50}$ values of compounds of formula I:

| Ex. | Compound of formula I | EC$_{50}$ (μM) |
|---|---|---|
| 1 | 9H-xanthene-9-carboxylic acid (4-trifluoromethyl-oxazol-2-yl)-amide | 0.056 |
| 2 | 9H-xanthene-9-carboxylic acid (5-trifluoromethyl-oxazol-2-yl)-amide | 0.038 |
| 3 | (RS)-2-fluoro-9H-xanthene-9-carboxylic acid (4-trifluoromethyl-oxazol-2-yl)-amide | 0.055 |
| 4 | (RS)-2-fluoro-9H-xanthene-9-carboxylic acid (5-trifluoromethyl-oxazol-2-yl)-amide | 0.020 |
| 5 | (RS)-3-fluoro-9H-xanthene-9-carboxylic acid (4-trifluoromethyl-oxazol-2-yl)-amide | 0.040 |
| 7 | (RS)-4-fluoro-9H-xanthene-9-carboxylic acid (4-trifluoromethyl-oxazol-2-yl)-amide | 0.016 |
| 8 | (RS)-4-fluoro-9H-xanthene-9-carboxylic acid (5-trifluoromethyl-oxazol-2-yl)-amide | 0.021 |
| 9 | 2,7-difluoro-9H-xanthene-9-carboxylic acid (4-trifluoromethyl-oxazol-2-yl)-amide | 0.044 |
| 10 | 2,7-difluoro-9H-xanthene-9-carboxylic acid (5-trifluoromethyl-oxazol-2-yl)-amide | 0.124 |
| 11 | 3,6-difluoro-9H-xanthene-9-carboxylic acid (4-trifluoromethyl-oxazol-2-yl)-amide | 0.003 |
| 12 | 3,6-difluoro-9H-xanthene-9-carboxylic acid (5-trifluoromethyl-oxazol-2-yl)-amide | 0.025 |
| 13 | (RS)-2-chloro-9H-xanthene-9-carboxylic acid (4-trifluoromethyl-oxazol-2-yl)-amide | 0.015 |
| 14 | (RS)-4-chloro-9H-xanthene-9-carboxylic acid (4-trifluoromethyl-oxazol-2-yl)-amide | 0.093 |

The compounds of formula I of the present invention are further characterized by high metabolic stability. This parameter is a prerequisite for good bioavailability, which is necessary to obtain medicaments with acceptable in-vivo activity. The metabolic stability has been tested by the following method:

Microsome Incubation

Incubation mixtures consisted of liver microsomes (rat 1.0 mg prot/mL or human 2.0 mg prot/mL), test compound 10 μM, MgCl$_2$ (3.3 mM), and an NADPH regenerating system consisting of glucose-6-phosphate dehydrogenase, NADPH and glucose-6-phosphate (equivalent to 1 mM NADPH) in a total volume of 1.0 mL of potassium phosphate buffer 100 mM pH 7.4. Reactions were initiated by addition of the NADPH regenerating system at 37° C. At the time of 1, 5, 9, 13, 17, 21, 25, and 29 min a 5 μL aliquot was directly analysed on a HPLC-MS/MS system consisting of a HP 1100 quaternary pump with degasser and a PE-Sciex API-2000 MS/MS spectrometer. The analytical column was a Waters Symmetry Shield RP8 (2.1*50 mm with a 3.5 μM particle size). A polarity non linear gradient from phase A (MeOH/Ac. Form.1% 20/80) to phase B (MeOH) was applied for a total run time of 2 minutes at a flow rate of 0.25 mL/min. The PE-Sciex API-2000 MS/MS spectrometer was used for detection of the parent compound. In vivo metabolic clearance was predicted according to published procedures [Houston, Biochem. Pharmacol. 47:1469–1479 (1994)]. In brief, the intrinsic clearance (Clearance, see table below) is calculated from the measured in vitro half-life taking into account incubation volume and microsomal protein used for the in vitro incubation. The intrinsic clearance is expressed in terms of μl/min/mg microsomal protein. For in vivo extrapolations, the hepatic extraction ratio (E) was calculated. Here it is reported the % MAB value which is equal to 1−E. The MAB (maximal achievable bioavailability) values express the maximal bioavailability that one can achieve with the given clearance values.

| Ex. | Intrinsic clearance (rat) (μl/min/mg) | MAB (rat) | Intrinsic clearance (human) (μl/min/mg) | MAB (human) |
|---|---|---|---|---|
| 1 | 108 | 25% | 8 | 68% |
| 2 | 50 | 37% | 14 | 68% |
| 3 | 61.4 | 32% | 9.9 | 61% |
| 4 | 40.2 | 43% | 18.8 | 45% |
| 5 | 34.3 | 46% | 4.3 | 78% |
| 6 | 27.8 | 52% | 9.2 | 63% |
| 7 | 32.8 | 48% | 7.9 | 67% |
| 8 | 31.8 | 49% | 19.2 | 45% |
| 9 | 8.9 | 77% | 2.7 | 85% |
| 10 | 26.1 | 54% | 5.6 | 73% |
| 11 | 17.6 | 63% | 11.1 | 59% |
| 12 | 11.6 | 72% | 9.1 | 63% |

The present invention also provides pharmaceutical compositions containing compounds of the invention or pharmaceutically acceptable salts thereof and a pharmaceutically acceptable carrier. Such pharmaceutical compositions can be in the form of tablets, coated tablets, dragées, hard and soft gelatine capsules, solutions, emulsions or suspensions. The pharamceutical compositions also can be in the form of suppositories or injection solutions.

The pharmaceutical compositions of the invention, in addition to one or more compounds of the invention or pharmaceutically acceptable salts thereof, contain a pharmaceutically acceptable carrier. "Pharmaceutically acceptable," such as pharmaceutically acceptable carrier, excipient, etc., means generally safe, substantially non-toxic, and neither biologically nor otherwise undesirable to the subject to which the particular compound is administered. Suitable pharmaceutically acceptable carriers include pharmaceutically inert, inorganic or organic carriers. Lactose, corn starch or derivatives thereof, talc, stearic acid or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like; depending on the nature of the active substance no carriers are, however, usually required in the case of soft gelatine capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula I, but as a rule are not necessary. Suitable carriers for suppositories are, for example, natural or hardened oils, waxes, fats, semi-liquid or liquid polyols and the like.

In addition, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

As mentioned earlier, the compounds of the present invention are mGlu 1 receptor agonists. Therefore, the present invention also provides methods of treating central nervous system diseases for which increased levels of L-glutamic acid are beneficial. In one embodiment, the present invention provides a method for treating Alzheimer's disease in an individual, which comprises administering to the individual, a therapeutically effective amount of a compound of formula I. In another embodiment, the present invention provides a method for treating Parkinson's disease in an individual, which comprises administering to the individual a therapeutically effective amount of a compound of formula I. In yet another embodiment, the present invention provides a method for treating Huntingdon chorea in an individual, which comprises administering to the individual a therapeutically effective amount of a compound of formula I. In a further embodiment, the present invention provides a method of treating amyotrophic lateral sclerosis (ALS) in an individual, which comprises administering to the individual a therapeutically effective amount of a compound of formula I. In a further embodiment, the present invention provides a method of treating dementia in an individual which comprises administering to the individual a therapeutically effective amount of a compound of formula I.

"Therapeutically effective amount" means an amount that is effective to prevent, alleviate or ameliorate symptoms of disease or prolong the survival of the subject being treated.

The dosages at which the compounds can be administered vary within wide limits and will, of course, be fitted to the individual requirements in each particular case. In general, the effective dosage for oral or parenteral administration is between 0.01–20 mg/kg/day, with a dosage of 0.1–10 mg/kg/day being preferred for all of the indications described. The daily dosage for an adult human being weighing 70 kg accordingly lies between 0.7–1400 mg per day, preferably between 7 and 700 mg per day.

Finally, as mentioned earlier, the use of compounds of formula I and of pharmaceutically acceptable salts thereof for the production of medicaments, especially for the control or prevention of acute and/or chronic neurological disorders of the aforementioned kind, is also an object of the invention.

In accordance with the foregoing the present invention also provides (1) A compound of formula I or a pharmaceutically acceptable salt thereof for use as a mGluR1 agonist, for example for use in any of the particular indications hereinbefore set forth;

(2) A pharmaceutical composition comprising a compound or salt as under (1) as active ingredient together with a pharmaceutically acceptable diluent or carrier therefore, for example for use in the treatment or prevention of a disease or condition in which mGluR 1 activation plays a role or is implicated;

(3) A method for the treatment of any of the particular indications hereinbefore set forth in a subject in need thereof which comprises administering an effective amount of a compound or salt as under (1);

(4) Use of a compound or salt as under (1) for the manufacture of a medicament for the treatment and prevention of diseases relating to the mGlu 1 receptor, for example a chronic neurological disorder.

(5) A process for the preparation of a compound or salt as under (1).

The following examples are provided for illustration of the invention. They should not be considered as limiting the scope of the invention, but merely as being representative thereof. Unless otherwise indicated, the following examples have been performed, regardless of the tense in which they are written.

EXAMPLE 1

9H-Xanthene-9-carboxylic acid (4-trifluoromethyl-oxazol-2-yl)-amide a) 4-Trifluoromethyl-oxazol-2-ylamine: The 4-trifluoromethyl-oxazol-2-ylamine is obtained using the procedure described in the literature [Crank and Foulis, J. Med. Chem. 14:1075 (1971)].

b) 9H-Xanthene-9-carboxylic acid (4-trifluoromethyl-oxazol-2-yl)-amide: To a solution of 150 mg (0.99 mmol, 1.0 equiv.) 4-trifluoromethyl-oxazol-2-ylamine and 6 mg (0.05 mmol, 0.05 equiv.) of N,N-dimethylamino pyridine in 2 ml of dry pyridine is added a solution of 245 mg (0.99 mmol) 9-xanthene-carboxylic acid chloride (CAS: [26454-53-5]) in 2 ml of methylene chloride dropwise at 0° C. The mixture is stirred 1 h at 0° C. and then at room temperature overnight. The mixture is poured into a well stirred mixture of 30 ml of methylene chloride and 30 ml of water. The organic phase is separated. The aqueous phase is extracted twice with 30 ml of methylene chloride. The combined organic phases are washed with 25 ml of water, dried over magnesium sulfate, and concentrated. The crude product (590 mg, yellow solid) yields, after recristallisation from ethyl acetate/hexane 250 mg (0.66 mmol, 66%) of 9H-xanthene-9-carboxylic acid (4-trifluoromethyl-oxazol-2-yl)-amide as white cristals, m.p. 222° C. and MS: m/e=361.2 (M+H$^+$).

EXAMPLE 2

9H-Xanthene-9-carboxylic Acid (5-trifluoromethyl-oxazol-2-yl)-amide a) 5-Trifluoromethyl-oxazol-2-ylamine: The 5-trifluoromethyl-oxazol-2-ylamine, off-white solid and MS: m/e=152.0 (M$^+$), is obtained using the following procedure: To a solution of 21.6 ml (39.4 g, 0.2 mol) of 97% 3-bromo-1,1,1-trifluoroacetone in 40 ml of tert-butanol are added 12.6 g (0.3 mol, 1.5 equiv.) of cyanamide. A slight exotherm is observed. After stirring for 10 min, 19.7 g (0.24 mol, 1.2 equiv.) of finely powdered sodium acetate were added with vigorous stirring and the suspension is heated for 30 min at 65° C., refluxed for 2 h and then allowed to cool. The mixture is poured into a well stirred mixture of 200 ml of ethyl acetate and 100 ml of water. The pH of the aqueous phase is set to ca. 8–9 with 5% sodium bicarbonate solution. The org. phase is separated. The aqueous phase is extracted with 50 ml ethyl acetate. The combined organic phases were washed twice with 20 ml of water and concentrated in vacuo. The residue, 40.2 g, viscous light orange oil, is then purified by flash chromatography on silica gel using a 2:1 mixture of methylene chloride and ethyl acetate as eluent. The fractions containing the desired compound (6.08 g, light yellow oil) and containing more polar impurities were concentrated and repurified by flash chromatography on silica gel using a 98:2 mixture of methylene chloride and methanol as eluent. One obtains 1.83 g (0.012 mol, 6%) of 5-trifluoromethyl-oxazol-2-ylamine.

b) 9H-Xanthene-9-carboxylic acid (5-trifluoromethyl-oxazol-2-yl)-amide: The title compound, white solid, m.p. 218° C. and MS: m/e=360.1(M$^+$), is prepared in accordance with the general method of example 1b from 5-trifluoromethyl-oxazol-2-ylamine and 9-xanthene-carboxylic acid chloride.

EXAMPLE 3

(RS)-2-Fluoro-9H-xanthene-9-carboxylic Acid (4-trifluoromethyl-oxazol-2-yl)-amide a) 2-Fluoro-9H-xanthene: To a solution of 19.63 g 2-fluoro-9-xanthone (CAS: [2839-49-8]) in 290 ml THF were added at room temperature 21.7 ml of borane dimethylsulfide complex. The mixture is refluxed for 4 h, and cooled to 5–10° C. 200 ml of methanol were added dropwise. An exotherm accompanied with foam and gas evolution is observed. The solution is evaporated to dryness, taken up in 200 ml of methanol and evaporated to dryness. The residue is taken up in 200 ml of ethyl acetate and evaporated to dryness. The crude product, 18.69 g beige solid, is purified by flash chromatography on silicagel using hexane as eluent. 17.97 g (89.8 mmol, 98%) of 2-fluoro-9H-xanthene are obtained as a white solid.

b) Racemic (RS)-2-Fluoro-9-xanthene-carboxylic acid: To a solution of 17.97 g fluoro-9H-xanthene in 285 ml of dry tetrahydrofurane is added at −70° C. to −65° C. 53.9 ml of a 2M solution of lithium diisopropylamide. The red solution is stirred for 20 min at −70° C., and then several pieces of dry ice are added to the mixture at −75° C. The red color rapidly disappears and the mixture is allowed to warm up to room temperature and stirred for 15 min. 250 ml of water are then added and stirring is maintained another 15 min. Ether (300 ml) is added to the mixture. The organic phase is extracted twice with 100 ml 2N sodium hydroxide solution and washed twice with 50 ml of water. The combined aqueous phases are washed with 25 ml of ether and then the pH is adjusted to 1–2 by addition of 27% hydrochloric acid solution. A white precipitate is formed. The acidified aqueous phase is extracted once with 300 ml of a 9:1 mixture of methylene chloride and methanol 9:1 and twice with 300 ml of methylene chloride. The combined organic phases are washed with 30 ml of water, dried over sodium sulfate and concentrated in vacuo. The crude product (12.87 g, beige solid) is triturated with ether to yield 11.78 g (48.2 mmol, 54%) of (RS)-2-fluoro-9-xanthene-carboxylic acid as white cristals, neg. ion MS: m/e=198.9 ((M−HCO2)$^-$.

c) (RS)-2-Fluoro-9H-xanthene-9-carboxylic acid (4-trifluoromethyl-oxazol-2-yl)-amide: To a solution of 883 mg (1.80 mmol, 1.1 equiv.) of 1,1'-carbonylbis(3-methylimidazolium) triflate (CBMIT) [Saha et al., J. Am. Chem. Soc. 111:4856 (1989)] in 3 ml of nitromethane at 10° C. are added 400 mg (1.64 mmol) of (RS)-2-fluoro-9-xanthene-carboxylic acid. The resulting suspension is allowed to warm up to room temperature and is stirred another 15 min. 4-Trifluoromethyl-oxazol-2-ylamine (274 mg, 1.80 mmol, 1.1 equiv.) is added and the mixture is stirred at room temperature for 16 h. The resulting light red viscous mixture is extracted with a mixture of 45 ml methylene chloride, 5 ml of methanol and 50 ml of water. The organic phase is separated. The aqueous phase is extracted twice with 30 ml methylene chloride/methanol 9:1. The combined organic phases are washed with 30 ml of water, dried over sodium sulfate and concentrated in vacuo. The crude product (630 mg, light red solid) is purified by flash chromatography on silicagel using methylene chloride as eluent. One obtains after recristallisation from ethyl acetate/hexane 233 mg (0.62 mmol, 38%) of (RS)-2-fluoro-9H-xanthene-9-carboxyl acid (4-trifluoromethyl-oxazol-2-yl)-amide as a white solid, m.p. 241° C. and MS: m/e=379.1(M+H$^+$).

EXAMPLE 4

(RS)-2-Fluoro-9H-xanthene-9-carboxylic Acid (5-trifluoromethyl-oxazol-2-yl)-amide The title compound, light yellow solid, m.p. 217° C. and neg. ion MS: m/e=377.1 (M−H$^-$), is prepared in accordance with the general method of example 3c from 5-trifluoromethyl-oxazol-2-ylamine and (RS)-2-fluoro-9-xanthene-carboxylic acid.

EXAMPLE 5

(RS)-3-Fluoro-9H-xanthene-9-carboxylic Acid (4-trifluoromethyl-oxazol-2-yl)-amide a) (RS)-3-Fluoro-9-xanthene-carboxylic acid: The racemic (RS)-3-fluoro-9-xanthene-carboxylic acid, white solid, neg. ion MS: m/e=198.9 ((M−HCO2)$^-$), is obtained in accordance with the general method of examples 3a and 3b from 3-fluoroxanthone (CAS:[2839-50-1]).

b) (RS)-3-Fluoro-9H-xanthene-9-carboxylic acid (4-trifluoromethyl-oxazol-2-yl)-amide: The title compound, light yellow solid, m.p. 221° C. and MS: m/e=379.1 (M+H$^+$) is prepared in accordance with the general method of example 3c from 5-trifluoromethyl-oxazol-2-ylamine and (RS)-3-fluoro-9-xanthene-carboxylic acid.

EXAMPLE 6

(RS)-3-Fluoro-9H-xanthene-9-carboxylic Acid (5-trifluoromethyl-oxazol-2-yl)-amide The title compound, white solid, m.p. 250° C. and neg. ion MS: m/e=377.1 (M−H$^-$) is prepared in accordance with the general method of example 3c from 5-trifluoromethyl-oxazol-2-ylamine and (RS)-3-Fluoro-9-xanthene-carboxylic acid.

EXAMPLE 7

(RS)-4-Fluoro-9H-xanthene-9-carboxylic Acid (4-trifluoromethyl-oxazol-2-yl)-amide a) (RS)-4-Fluoro-9-xanthene-carboxylic acid: The racemic (RS)-4-fluoro-9-xanthene-carboxylic acid, white solid, neg. ion MS: m/e=198.9 ((M−HCO2)$^-$) is obtained in accordance with the general method of examples 3a and 3c from 4-fluoroxanthone (CAS:[2839-51-2]).

b) (RS)-4-Fluoro-9H-xanthene-9-carboxylic acid (4-trifluoromethyl-oxazol-2-yl)-amide: The title compound, white solid, m.p. 233° C. and MS: m/e=379.2 (M+H$^+$) is prepared in accordance with the general method of example 3c from 4-trifluoromethyl-oxazol-2-ylamine and (RS)-4-fluoro-9-xanthene-carboxylic acid.

EXAMPLE 8

(RS)-4-Fluoro-9H-xanthene-9-carboxylic Acid (5-trifluoromethyl-oxazol-2-yl)-amide The title compound, white solid, m.p. 228° C. and MS: m/e=379.2 (M+H$^+$) is prepared in accordance with the general method of example 3c from 5-trifluoromethyl-oxazol-2-ylamine and (RS)-4-fluoro-9-xanthene-carboxylic acid.

EXAMPLE 9

2,7-Difluoro-9H-xanthene-9-carboxylic Acid (4-trifluoromethyl-oxazol-2-yl)-amide The title compound, white solid, m.p. 259° C. and MS: m/e=397.1 (M+H$^+$), is prepared in accordance with the general method of example 3c from 4-trifluoromethyl-oxazol-2-ylamine and 2,7-difluoro-9H-xanthene-9-carboxylic acid (CAS:[188028-26-4]).

EXAMPLE 10

2,7-Difluoro-9H-xanthene-9-carboxylic Acid (5-trifluoromethyl-oxazol-2-yl)-amide The title compound, white solid, m.p. 232° C. and neg. ion MS: m/e=395.1 (M−H$^-$), is prepared in accordance with the general method of example 3c from 5-trifluoromethyl-oxazol-2-ylamine and 2,7-difluoro-9H-xanthene-9-carboxylic acid.

EXAMPLE 11

3,6-Difluoro-9H-xanthene-9-carboxylic Acid (4-trifluoromethyl-oxazol-2-yl)-amide The title compound, white solid, m.p. 265° C. and MS: m/e=397.2 (M+H$^+$), is prepared in accordance with the general method of example 3c from 4-trifluoromethyl-oxazol-2-ylamine and 3,6-difluoro-9H-xanthene-9-carboxylic acid (CAS:[188028-37-7]).

EXAMPLE 12

3,6-Difluoro-9H-xanthene-9-carboxylic Acid (5-trifluoromethyl-oxazol-2-yl)-amide The title compound, white solid, m.p. 249° C. and MS: m/e=379.2 (M+H$^+$), is prepared in accordance with the general method of example 3c from 5-trifluoromethyl-oxazol-2-ylamine and 3,6-difluoro-9H-xanthene-9-carboxylic acid.

EXAMPLE 13

(RS)-2-Chloro-9H-xanthene-9-carboxylic Acid (4-trifluoromethyl-oxazol-2-yl)-amide The title compound, white solid, m.p. 235° C. and MS: m/e=395.2, 397.2 (M+H$^+$) is prepared in accordance with the general method of example 3c from 4-trifluoromethyl-oxazol-2-ylamine and (RS)-2-chloro-9H-xanthene-9-carboxylic acid (CAS:[188027-67-0]).

EXAMPLE 14

(RS)-4-Chloro-9H-xanthene-9-carboxylic Acid (4-trifluoromethyl-oxazol-2-yl)-amide The title compound, white solid, m.p. 212° C. and MS: m/e=395.1, 397.1 (M+H$^+$) is prepared in accordance with the general method of example 3c from 5-trifluoromethyl-oxazol-2-ylamine and (RS)-4-chloro-9H-xanthene-9-carboxylic acid (CAS:[188027-87-4]).

The following Examples A to C are prophetic.

EXAMPLE A

Tablets

Tablets (250 mg) of the following composition are produced in a conventional manner:

|  | mg/Tablet |
|---|---|
| Active ingredient | 100 |
| Powdered. lactose | 95 |
| White corn starch | 35 |
| Polyvinylpyrrolidone | 8 |
| Na carboxymethylstarch | 10 |
| Magnesium stearate | 2 |

EXAMPLE B

Tablets

Tablets (400 mg) of the following composition are produced in a conventional manner:

|  | mg/Tablet |
|---|---|
| Active ingredient | 200 |
| Powdered. lactose | 100 |
| White corn starch | 64 |
| Polyvinylpyrrolidone | 12 |
| Na carboxymethylstarch | 20 |
| Magnesium stearate | 4 |

EXAMPLE C

Capsules

Capsules (fill weight 150 mg) of the following composition are produced:

|  | mg/Capsule |
|---|---|
| Active ingredient | 50 |
| Crystalline. lactose | 60 |
| Microcrystalline cellulose | 34 |
| Talc | 5 |
| Magnesium stearate | 1 |

The active ingredient having a suitable particle size, the crystalline lactose and the microcrystalline cellulose are homogeneously mixed with one another, sieved and thereafter talc and magnesium stearate are admixed. The final mixture is filled into hard gelatine capsules of suitable size.

The invention claimed is:

1. A compound of formula I

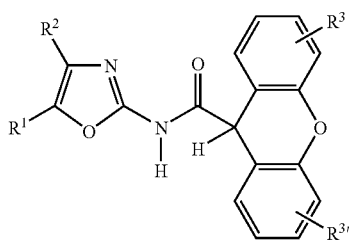

wherein
one of $R^1$ and $R^2$ is trifluoromethyl, and the other is hydrogen;
$R^3$ and $R^{3'}$ are each independently hydrogen or halogen; or a pharmaceutically acceptable salt thereof.

2. A compound of formula I according to claim 1, wherein $R^3$ and $R^{3'}$ are both hydrogen.

3. A compound of formula I according to claim 1, wherein $R^1$ is trifluoromethyl and $R^2$ is hydrogen.

4. A compound of formula I according to claim 1, wherein $R^1$ is trifluoromethyl, $R^2$ is hydrogen, and at least one of $R^3$ and $R^{3'}$ is halogen.

5. A compound of formula I according to claim 4, wherein at least one of $R^3$ and $R^{3'}$ is fluoro.

6. A compound of formula I according to claim 4 wherein at least one of $R^3$ and $R^{3'}$ is chloro.

7. A compound of formula I according to claim 1, wherein $R^1$ is hydrogen and $R^2$ is trifluoromethyl.

8. A compound of formula I according to claim 1, wherein $R^1$ is hydrogen, $R^2$ is trifluoromethyl, and at least one of $R^3$ and $R^{3'}$ is halogen.

9. A compound of formula I according to claim 8, wherein at least one of $R^3$ and $R^{3'}$ is fluoro.

10. A compound of formula I according to claim 8, wherein at least one of $R^3$ and $R^{3'}$ is chloro.

11. A compound of formula I according to claim 1, selected from
9H-xanthene-9-carboxylic acid (4-trifluoromethyl-oxazol-2-yl)-amide,
9H-xanthene-9-carboxylic acid (5-trifluoromethyl-oxazol-2-yl)-amide,
2-fluoro-9H-xanthene-9-carboxylic acid (5-trifluoromethyl-oxazol-2-yl)-amide, and
3-fluoro-9H-xanthene-9-carboxylic acid (5-trifluoromethyl-oxazol-2-yl)-amide.

12. A compound of formula I according to claim 1, selected from
4-fluoro-9H-xanthene-9-carboxylic acid (5-trifluoromethyl-oxazol-2-yl)-amide,
2,7-difluoro-9H-xanthene-9-carboxylic acid (5-trifluoromethyl-oxazol-2-yl)-amide,
3,6-difluoro-9H-xanthene-9-carboxylic acid (5-trifluoromethyl-oxazol-2-yl)-amide, and
2-fluoro-9H-xanthene-9-carboxylic acid (4-trifluoromethyl-oxazol-2-yl)-amide.

13. A compound of formula I according to claim 1, selected from
3-fluoro-9H-xanthene-9-carboxylic acid (4-trifluoromethyl-oxazol-2-yl)-amide,3-fluoro-9H-xanthene 9-carboxylic acid (4-trifluoromethyl-oxazol-2-yl)-amide, and
2,7-difluoro-9H-xanthene-9-carboxylic acid (4-trifluoromethyl-oxazol-2-yl)-amide.

14. A compound of formula I according to claim 1, selected from
3,6-difluoro-9H-xanthene-9-carboxylic acid (4-trifluoromethyl-oxazol-2-yl)-amide,
2-chloro-9H-xanthene-9-carboxylic acid (4-trifluoromethyl-oxazol-2-yl)-amide, and
4-chloro-9H-xanthene-9-carboxylic acid (4-trifluoromethyl-oxazol-2-yl)-amide.

15. A composition comprising a compound of formula I

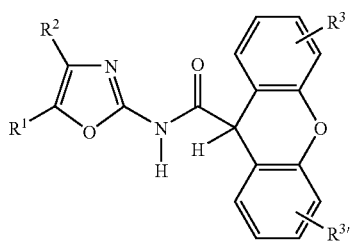

wherein
one of $R^1$ and $R^2$ signifies trifluoromethyl, and the other one signifies hydrogen;
$R^3$, $R^{3'}$ signify, independently from each other, hydrogen or halogen;
or a pharmaceutically acceptable salt thereof and a pharmaceutically acceptable carrier.

16. A process for preparing a compound of formula I according to claim 1, which process comprises reacting a compound of formula II

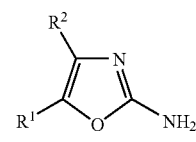

wherein one of $R^1$ and $R^2$ signifies trifluoromethyl, and the other one signifies hydrogen, with a compound of formula III

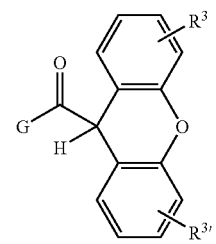

wherein $R^3$ and $R^{3'}$ signify, independently from each other, hydrogen or halogen, and G signifies chloro or hydroxy.

17. A method of treating Alzheimer's disease in an individual, comprising administering to the individual an effective amount of a compound of formula I.

18. A method of treating Parkinson's disease in an individual, comprising administering to the individual an effective amount of a compound of formula I.

19. A method of treating dementia in an individual, comprising administering to the individual an effective amount of a compound of formula I.

20. A method of treating amyotrophic lateral sclerosis (ALS) in an individual, comprising administering to the individual an effective amount of a compound of formula I.

21. A method of treating Huntingdon chorea in an individual, comprising administering to the individual an effective amount of a compound of formula I.

* * * * *